US010010263B2

(12) United States Patent
Cao et al.

(10) Patent No.: US 10,010,263 B2
(45) Date of Patent: Jul. 3, 2018

(54) TECHNOLOGY FOR ROBUST REGIONAL AND GLOBAL LIVER FUNCTION QUANTIFICATION FROM CLINICAL MULTI-PHASE MRI

(71) Applicant: THE REGENTS OF THE UNIVERSITY OF MICHIGAN, Ann Arbor, MI (US)

(72) Inventors: Yue Cao, Ann Arbor, MI (US); Josiah J. Simeth, Ann Arbor, MI (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 0 days.

(21) Appl. No.: 15/822,652

(22) Filed: Nov. 27, 2017

(65) Prior Publication Data

US 2018/0146880 A1 May 31, 2018

Related U.S. Application Data (60) Provisional application No. 62/426,831, filed on Nov. 28, 2016.

(51) Int. Cl.
| | |
|---|---|
| *G06K 9/00* | (2006.01) |
| *A61B 5/055* | (2006.01) |
| *G01R 33/56* | (2006.01) |
| *A61B 5/00* | (2006.01) |
| *G01R 33/30* | (2006.01) |
| *G01R 33/24* | (2006.01) |

(52) U.S. Cl.
CPC ............ *A61B 5/055* (2013.01); *A61B 5/4244* (2013.01); *G01R 33/5601* (2013.01); *G01R 33/246* (2013.01); *G01R 33/30* (2013.01); *G01R 33/5608* (2013.01)

(58) Field of Classification Search
None
See application file for complete search history.

(56) References Cited

PUBLICATIONS

Yamada, "Quantitative Evaluation of Liver Function Within MR Imaging," Abdomen and Thoracic Imaging, pp. 233-251 (2014).
Johnson et al., "Assessment of Liver Function in Patients With Hepatocellular Carcinoma: A New Evidence-Based Approach—The ALBI Grade," Journal of Clinical Oncology (2015).
Sourbron et al., "Combined Quantification of Liver Perfusion and Function with Dynamic Gadoxetic Acid-Enhanced MR Imaging," Radiology, vol. 263 (2012).

*Primary Examiner* — Atiba O Fitzpatrick
(74) *Attorney, Agent, or Firm* — Marshall, Gerstein & Borun LLP; Randall G. Rueth (57) ABSTRACT

A robust liver function quantification algorithm to quantify regional and global liver function using temporally sparse-sampled multi-phase MRI with gadoxetic-acid injection is provided. The liver function quantification algorithm may be utilized in a liver function analysis server and indications of a patient's liver function may be provided for display on a healthcare professional's network-enabled device. The use of a single clinical multi-phase MRI with gadoxetic-acid injection may provide 1) regional liver function assessment, 2) global liver function assessment, and 3) risk analysis for future liver intervention.

20 Claims, 7 Drawing Sheets

TECHNOLOGY FOR ROBUST REGIONAL AND GLOBAL LIVER FUNCTION QUANTIFICATION FROM CLINICAL MULTI-PHASE MRI

CROSS-REFERENCE TO RELATED APPLICATIONS

The present disclosure claims the benefit of U.S. Provisional Patent Application No. 62/426,831, entitled "Technology for Robust Regional and Global Liver Function Quantification from Clinical Multi-Phase MRI" filed on Nov. 28, 2016, the disclosure of which is expressly incorporated by reference herein in its entirety.

STATEMENT OF GOVERNMENTAL INTEREST

This invention was made with government support under grant no. CA132834 awarded by the National Institutes of Health. The government has certain rights in the invention.

TECHNICAL FIELD

The present application relates to liver function quantification and, more specifically, to a method and system for a robust algorithm to quantify regional and global liver function from clinical multi-phase magnetic resonance imaging (MRI) with gadoxetic-acid to support risk assessment of liver function.

BACKGROUND

Recent studies show that liver function is a predominant predictor for overall survival for patients with intrahepatic cancer and cirrhosis regardless of intervention (Johnson, J C O 2015). There is no robust method to quantify regional liver function from the routine clinical multi-phase MRI with gadoxetic-acid injection. Current techniques, including the deconvolution technique, cannot differentiate contrast agents in hepatocytes from in the blood plasma, the first indicates the liver function (capability of uptake of contrast agents) and the latter is related to the hemodynamics of agents in the blood. The dual-input two-compartment model (Sourbron, Radiology 2012) requires fitting six unknown parameters (5 involving hemodynamics of the liver blood flow) and typically requires acquisition of high-temporal resolution dynamic gadoxetic-acid enhanced (DGAE) MRI. The acquisition of high-temporal resolution DGAE MRI challenges routine workflow at a typical MRI clinic and is time consuming when fitting a long dynamic series of data in the whole liver. Due to temporally sparse-sampling in routine clinical multi-phase MRI with gadoxetic-acid injection, the arterial ($C_a$) and portal vein ($C_{pv}$) input functions that are required to fit the dual-input two-compartment model cannot be determined accurately, resulting in a large uncertainty and variation in the fitted parameters. As a result, a semi-quantitative analysis is performed that cannot differentiate intra- and extra-cellular contrasts.

SUMMARY

A robust liver function quantification algorithm is described to quantify regional and global liver function using temporally sparse-sampled multi-phase MRI with gadoxetic-acid injection is presented. Using regional liver function maps created by this technique, a healthcare professional may assess the risk of liver function failure or liver function preserve (e.g., functional volume) for treatment decisions before and during intrahepatic cancer therapy. Additionally, a liver surgeon may utilize the liver function quantification algorithm to estimate liver function preserve after resection of a segment of the liver. While the dual-input two-compartment model requires fitting six unknown parameters which requires high-temporal resolution images, the liver function quantification algorithm described below fits two unknown parameters (a contrast uptake rate and a fractional distribution volume) in a linear liver pharmacokinetic model (i.e., the unknown parameters have a linear relationship). Accordingly, the present embodiments advantageously increase the computational speed required to quantify liver function. The liver function quantification algorithm is approximately 1000 times faster than the dual-input two-compartment model.

For the purposes of diagnosis of intrahepatic cancer and management of liver function, temporally sparse-sampled multi-phase MRI with gadoxetic-acid injection is acquired routinely in patients with liver diseases (including cirrhosis). Temporally sparse-sampled multi-phase MRI typically consists of 6 dynamic-phase MRI volumes. The liver function quantification algorithm described herein uses a single clinical test (clinical multi-phase MRI with gadoxetic-acid injection) including the 6 dynamic-phase MRI volumes to provide 1) regional liver function assessment, 2) global liver function assessment (e.g., liver function volume), and 3) risk analysis for future liver intervention (e.g., the liver functional volume preserve after a segment or lobe resection of the liver or regional and global liver function response to future radiation doses based upon current individual patient responses to doses). The regional and global liver function assessments are then provided to a healthcare professional's network-enabled device or treatment planning and navigation systems as indications of the patient's liver function.

In one aspect, a computer-implemented method for quantifying liver function in a patient is provided. The method may include obtaining one or more three-dimensional (3-D) images of a patient's liver, the one or more 3-D images collected using magnetic resonance imaging (MRI), positron emission tomography (PET), or single-photon emission computed tomography (SPECT); and for each of the one or more 3-D images: analyzing the 3-D image to identify a plurality of contrast concentration parameters collected over time; generating a linear liver pharmacokinetic model using the plurality of contrast concentration parameters collected over time; calculating a contrast uptake rate metric for liver cells and a fractional distribution volume for the blood based on the linear liver pharmacokinetic model, wherein the contrast uptake rate metric is indicative of liver function in the patient; and displaying an indication of the contrast uptake rate metric to provide an assessment of the liver function in the patient to a healthcare professional.

In another aspect, a computing device for quantifying liver function in a patient is provided. The computing device includes a communication network, one or more processors, and a non-transitory computer-readable memory coupled to the one or more processors and storing instructions thereon. When executed by the one or more processors, the instructions cause the system to obtain one or more three-dimensional (3-D) images of a patient's liver, the one or more 3-D images collected using magnetic resonance imaging (MRI), positron emission tomography (PET), or single-photon emission computed tomography (SPECT); and for each of the one or more 3-D images: analyze the 3-D image to identify a plurality of contrast concentration parameters collected over time; generate a linear liver pharmacokinetic model using the plurality of contrast concentration parameters collected over time; calculate a contrast uptake rate metric for liver cells and a fractional distribution volume for the blood based on a linear liver pharmacokinetic model, wherein the contrast uptake rate metric is indicative of liver function in the patient; and display an indication of the contrast uptake rate metric to provide an assessment of the liver function in the patient to a healthcare professional.

DETAILED DESCRIPTION

Although the following text sets forth a detailed description of numerous different embodiments, it should be understood that the legal scope of the description is defined by the words of the claims set forth at the end of this disclosure. The detailed description is to be construed as exemplary only and does not describe every possible embodiment since describing every possible embodiment would be impractical, if not impossible. Numerous alternative embodiments could be implemented, using either current technology or technology developed after the filing date of this patent, which would still fall within the scope of the claims.

It should also be understood that, unless a term is expressly defined in this patent using the sentence "As used herein, the term '________' is hereby defined to mean . . . ." or a similar sentence, there is no intent to limit the meaning of that term, either expressly or by implication, beyond its plain or ordinary meaning, and such term should not be interpreted to be limited in scope based on any statement made in any section of this patent (other than the language of the claims). To the extent that any term recited in the claims at the end of this patent is referred to in this patent in a manner consistent with a single meaning, that is done for sake of clarity only so as to not confuse the reader, and it is not intended that such claim term be limited, by implication or otherwise, to that single meaning. Finally, unless a claim element is defined by reciting the word "means" and a function without the recital of any structure, it is not intended that the scope of any claim element be interpreted based on the application of 35 U.S.C. § 112, sixth paragraph.

Generally speaking, techniques for liver function analysis may be implemented in one or more network enabled devices, one or more network servers, or a system that includes a combination of these devices. However, for clarity, the examples below focus primarily on an embodiment in which a liver function analysis server obtains a set of image data for a patient's liver or a portion thereof. In some embodiments, the set of image data may be obtained from a network enabled MRI, positron emission tomography (PET), or single-photon emission computed tomography (SPECT) machine or picture archiving and communication system (PACS) containing MR image data, PET image data, or SPECT image data. In other embodiments, the set of image data may be received from other network enabled devices that may have image data stored in memory. For example, the set of image data may be stored in memory on a laptop computer, a desktop computer, a smart phone, a network-enabled cell phone, a wearable computing device, etc. The set of image data may be communicated over a wired and/or wireless network to a network-enabled server such as the liver function analysis server. Additionally, the liver function analysis server may obtain the set of image data from a wired or wireless communication with network-enabled devices.

After the liver function analysis server obtains the set of image data from a network-enabled device, the set of image data may be accessed by a liver function quantification module. The liver function quantification module may apply the liver function quantification algorithm in order to determine a contrast uptake rate metric that is indicative of liver function. The contrast uptake rate metric may be a normalized rate of uptake of contrast to an intercellular volume ($k_1$). The liver function quantification module may also have access to additional data such as contrast concentration parameter values required for the liver function quantification algorithm to calculate the contrast uptake rate metric. Then an indication of the contrast uptake rate metric may be provided to a network-enabled device of a healthcare professional. For example, regional liver function maps and global liver function metrics may be generated based on the contrast uptake rate metric. Each regional liver function map is comprised of an array of voxels. The regional liver function maps may be displayed on the network-enabled device and each voxel may be color-coded to show the differences in the function intensity for each voxel throughout the map. The differences in function intensity from voxel to voxel may be representative of variations of the contrast uptake rate metric throughout the regional volume of the liver or the whole liver.

Similarly, the aspects described herein also provide improvements to various technical fields. Namely, these technical fields include data collection, image processing and analysis, and the displaying of processed images. Instead of merely being performed by hardware components using basic functions, the aspects described herein employ a unique combination of complex steps that go beyond the mere concept of simply retrieving and combining data using a computer.

In particular, the hardware components described herein may perform various functions that include, for example, capturing of clinical multi-phase MRI data, processing and analyzing the clinical multi-phase MRI data, and displaying the clinical multi-phase MRI image via an electronic device. The clinical multi-phase MRI images that are displayed on the electronic device may include areas of different contrast in order to indicate differences from one portion of the image to another. The clinical multi-phase MRI images may also include a key to indicate the meaning of each level of contrast.

Additionally, as mentioned above, the liver function quantification algorithm fits two unknown parameters as opposed to six unknown parameters for the dual-input two-compartment model and thus is 1000 times faster than the dual-input two-compartment model. As a result, the aspects described herein may also support dynamic, real-time, or near real-time analysis of captured and received data. In particular, an electronic device (e.g., a desktop computer) may receive clinical multi-phase MRI data in real-time or near real-time, and may analyze and process the clinical multi-phase MRI data in real-time or near real-time. In this regard, physicians and patients are afforded the benefit of an accurate representation of a patient's liver function as it is when the clinical multi-phase MRI is taken.

Figure 1:
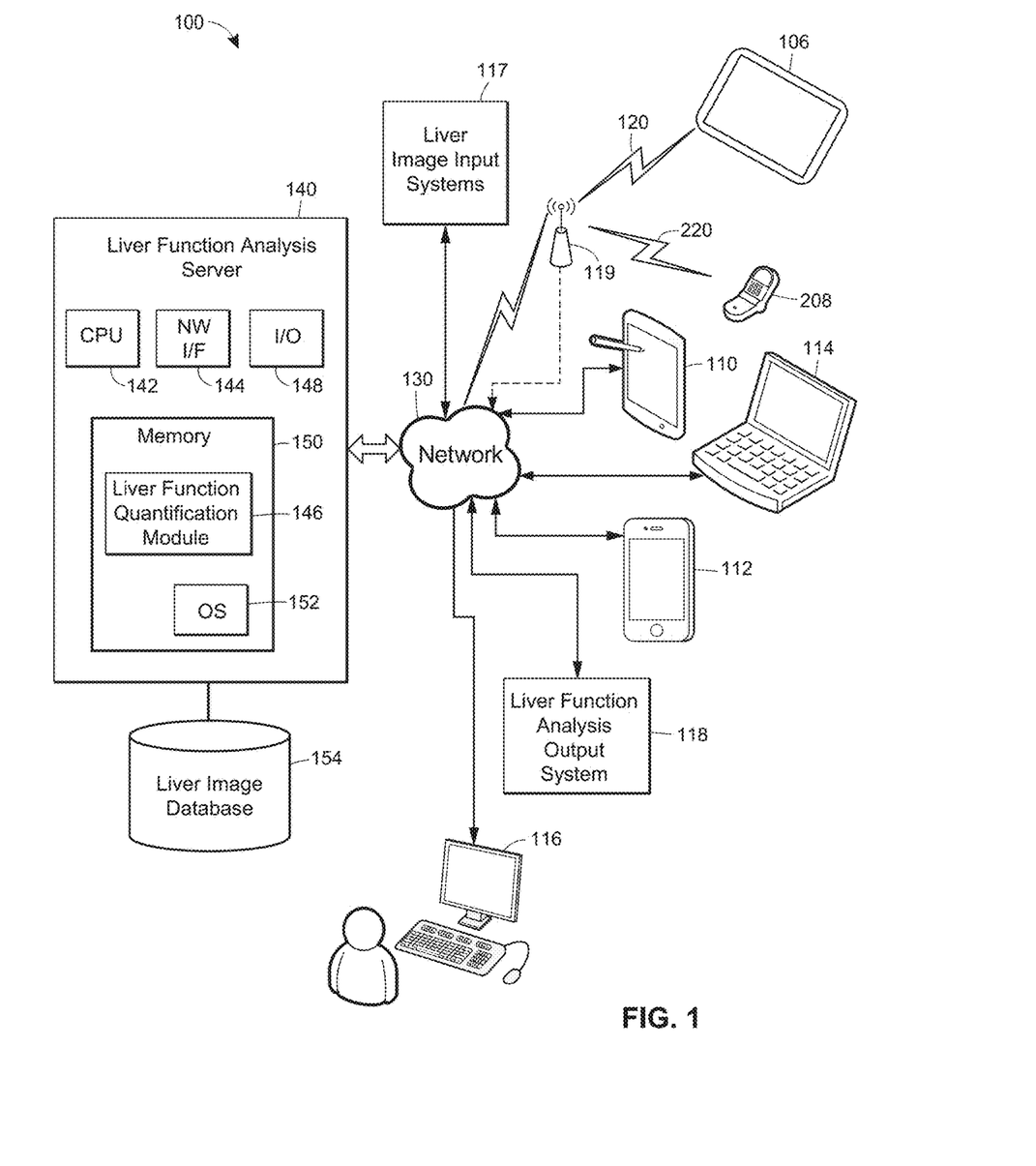
FIG. 1 illustrates a block diagram of a computer network and system of which an exemplary liver function analysis system for liver function quantification may operate in accordance with the presently described embodiments.

Referring to FIG. 1, an example liver function analysis system 100 for liver function quantification in which the techniques outlined above can be implemented includes a liver function analysis server 140, and one or more network-enabled devices 106-118 which may be utilized by healthcare professionals, for example. In an embodiment, the liver function analysis server 140 and the one or more network-enabled devices 106-118 may communicate via wireless signals 120 over a communication network 130, which can be any suitable local or wide area network(s) including a Wi-Fi network, a Bluetooth network, a cellular network such as 3G, 4G, Long-Term Evolution (LTE), the Internet, etc. In some instances, the network-enabled devices 106-118 may communicate with the communication network 130 via an intervening wireless or wired device 119, which may be a wireless router, a wireless repeater, a base transceiver station of a mobile telephony provider, etc. The network-enabled devices 106-118 may include, by way of example, a tablet computer 106, a network-enabled cell phone 108, a personal digital assistant (PDA) 110, a mobile device smart-phone 112 also referred to herein as a "mobile device," a laptop computer 114, a desktop computer 116, one or several types of liver image input systems (e.g., MRI machine, PACS, etc.) 117, one or several types of liver function analysis output systems (as described below) 118, a portable media player (not shown), a wearable computing device such as Google Glass™ (not shown), etc. Examples of liver function analysis output systems 118 are: radiation treatment planning systems, surgery planning and navigational systems, and other liver intervention planning and navigation systems (e.g., radio frequency ablation (RFA), microwave ablation, and high-intensity focused ultrasound (HIFU)). Moreover, any other suitable network-enabled device that stores image data or is capable of receiving communication messages may also communicate with the liver function analysis server 140.

Each of the network-enabled devices 106-118 may interact with the liver function analysis server 140 to transmit image data and/or receive indications of the contrast uptake rate metric or any other suitable metric indicative of liver function. In an example implementation, the liver function analysis server 140 may be a cloud based server, an application server, a web server, etc., and includes a memory 150, one or more processors (CPU) 142, a network interface unit 144, and an I/O module 148.

The liver function analysis server 140 is also communicatively connected to a liver image database 154. The liver image database 154 may include one or more types of data associated with liver images. For example, the liver image database 154 may include liver images from MRI scans, PET scans, or SPECT scans that have occurred in the past.

The memory 150 may be tangible, non-transitory memory and may include any types of suitable memory modules, including random access memory (RAM), read only memory (ROM), flash memory, other types of persistent memory, etc. The memory 150 stores an operating system (OS) 152 and one or more modules including a liver function quantification module 146. The operating system 152 may be any type of suitable operating system such as modern smartphone operating systems, for example. Also, the I/O module 148 may be a keyboard or a touchscreen, for example.

The liver function quantification module 146 may receive image data from a network-enabled device 106-118. For example, a patient may take an MRI scan of the liver and after the MRI scan is complete the MRI machine (which is one of the several types of liver image input systems 117) may transmit the MR image data obtained from the MRI scan to the liver function analysis server 140. The liver function quantification module 146 may then access the MR image data and apply the liver function quantification algorithm in order to determine the contrast uptake rate metric used to generate regional and global liver maps that are indicative of liver function. Moreover, the results generated by the liver function quantification module 146 (e.g., contrast uptake rate metric, regional and global liver maps, etc.) may be transmitted to one or more network-enabled devices 106-118 via the communication network 130. These results can be stored in the memory of the network-enabled device(s) 106-118 or the liver image database 154 and/or displayed on the screen of the network-enabled device(s) 106-118.

Figure 2:
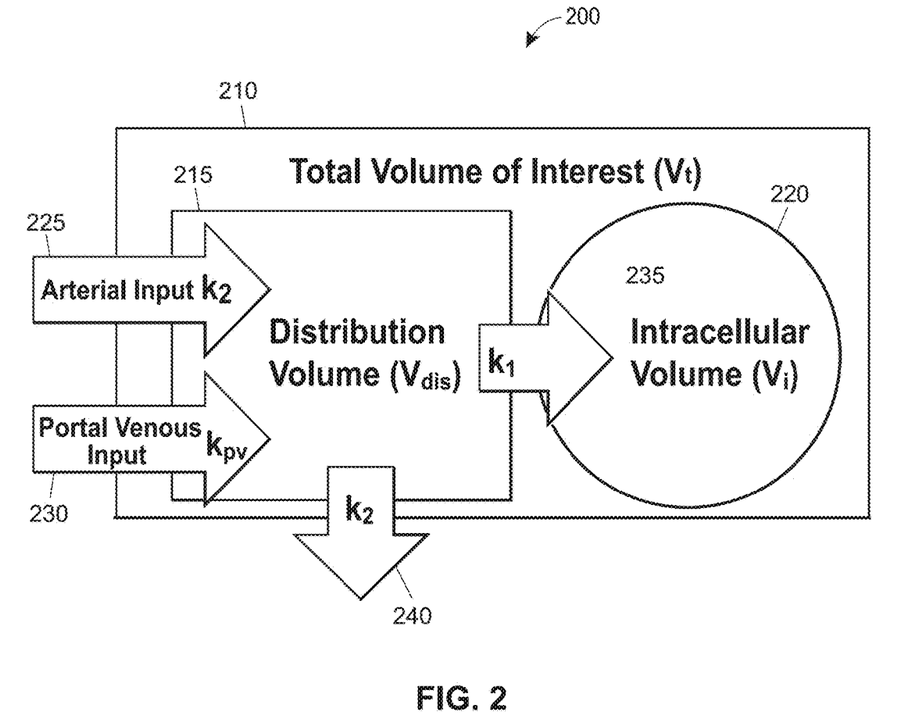
FIG. 2 illustrates an exemplary dual-input two-compartment pharmacokinetic model of gadoxetic-acid in the liver.

As described above, the dual-input two-compartment model uses DGAE MRI which can be accomplished through the use of an MRI machine such as the MRI machine that is one of the liver image input systems 117. DGAE MRI allows quantification of regional hepatic perfusion and liver function through observation of hemodynamics and uptake of contrast agent in the blood vessels and parenchyma, respectively. The hepatic perfusion and contrast uptake rate ($k_1$) may be quantified through the dual-input two-compartment model (Sourbron, Radiology 2012), which is illustrated by the diagram 200 of FIG. 2 and described by the following equations:

$$\underbrace{\frac{Contrast\ in\ Tissue}{V_t C_t(t)}} = \underbrace{\frac{Exctracellular\ Contrast}{V_{dis} C_{dis}(t)}} + k_1 \int_0^t \overbrace{V_{dis} C_{dis}(\tau)}^{Intracellular\ Contrast} d\tau \quad (1)$$

$$V_{dis} C_{dis}(t) = V_{dis} \int_0^t ((k_a C_a(\tau - \tau_a) + k_{pv} C_{pv}(\tau - \tau_{pv}))e^{-(t-\tau)(k_2+k_1)}) d\tau \quad (2)$$

where $V_{dis}$ is the distribution volume 215 of blood; $C_t$, $C_{dis}$, $C_a$, and $C_{pv}$ are contrast concentrations as a function of time in the respective total, distribution (defined below), arterial, and portal vein volumes; $\tau_a$ and $\tau_{pv}$ describe respective arrival time delays of the arterial and portal vein input functions at each voxel; $k_a$ 225 and $k_{pv}$ 230 describe the normalized arterial and portal venous flow rates, and $k_2$ 240 is the normalized flow rate leaving the volume of interest ($V_t$) 210 through the central vein. $k_1$ 235 is the normalized rate of uptake of contrast to the intercellular volume ($V_i$) 220. The distribution volume 215 includes the Space of Disse (perisinusoidal space) and sinusoids. Also, the definition of the fractional distribution volume is $$v_{dis} = \frac{V_{dis}}{V_t}.$$

In Eqs [1] and [2], six unknown parameters ($k_a$, $k_{pv}$, $k_2$, $\tau_a$, $\tau_{pv}$ and $k_1$) need to be fitted as mentioned above. Fitting these unknown parameters (5 involving hemodynamics of the liver blood flow) typically requires acquisition of high-temporal resolution (3-4 s per volume) dynamic contrast enhanced MRI for up to 20 minutes after gadoxetic-acid injection. This type of acquisition is challenging for routine integration within the workflow of a typical MRI clinic. In addition, optimizing the 6 parameters is susceptible to overfitting of variations in the dynamic gadoxetic-acid enhanced MRI caused by noise and respiratory motion, and is time consuming when fitting a long dynamic series of data in the whole liver (that contains 600,000-1,000,000 voxels).

Figure 3:
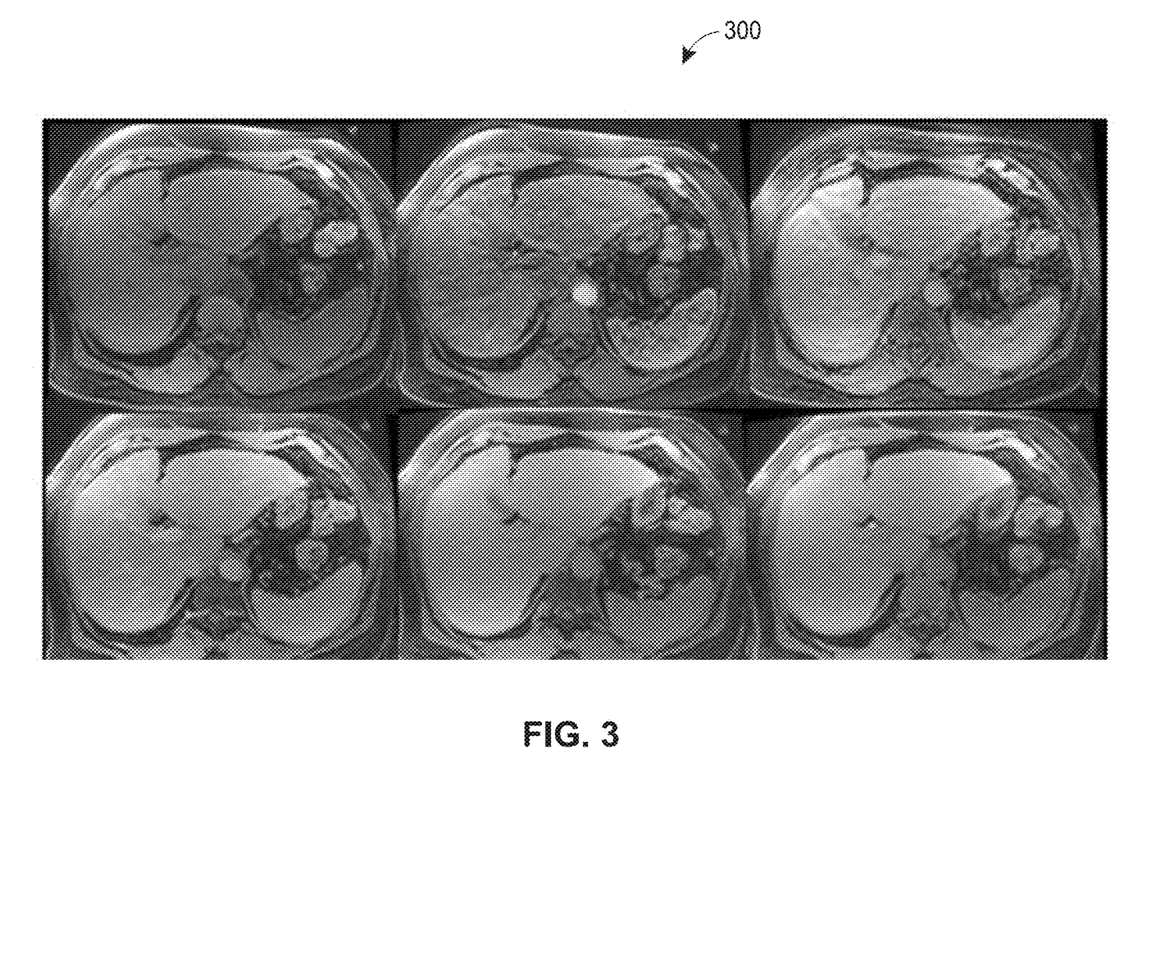
FIG. 3 illustrates exemplary cross-sectional images of pre-contrast, arterial phase, portal vein phase, late portal vein phase, 10 min., and 20 min. after gadoxetic-acid injection (in an order from left to right and from the first row to the second row).

On the other hand, temporally sparse-sampled multi-phase MRI with gadoxetic-acid injection is routinely acquired in the MRI clinics worldwide. In these MRI exams, typically 6 dynamic-phase MRI volumes are acquired: pre-contrast, arterial phase (~20 s), portal vein phase (~40 s), late portal vein phase (~60 s), 5-10 minutes, and 20 minutes after contrast injection, as shown in diagram 300 in FIG. 3.

To quantify liver function in a patient, the liver function quantification module 140 determines a contrast uptake rate metric ($k_1$) from the temporally sparse sampled clinical multi-phase MRI scans with gadoxetic-acid injection using a liver function quantification algorithm. Additionally, indications of the contrast uptake rate metric ($k_1$) such as liver functions maps ($k_1$ maps) may be generated. In some embodiments, $k_1$ maps may include a representation of the $k_1$ value at each voxel of an MR image of the liver. The MR images from the temporally sparse sampled clinical multi-phase MRI scans with gadoxetic-acid injection may be transmitted from the MRI machine (or other liver image input system 117 as described above) to the liver function analysis server 140. The liver function quantification module 146 may access the images from the liver function analysis server 140 in order to apply the liver function quantification algorithm.

Liver Function Quantification Algorithm

To generate the liver function quantification algorithm, Eq [2] may be re-written in a derivative form:

$$V_{dis}\frac{dC_{dis}(t)}{dt} = F_{ap}C_{ap}(t-\tau_a) + F_{pvp}C_{pvp}(t-\tau_{pv}) - (F_{ap} + F_{pvp} + K_1)C_{dis}(t) \quad (3)$$

where $F_{ap}$, and $F_{pvp}$ are the total amounts of arterial blood plasma flow and portal vein blood plasma flow in the distribution space in the voxel, respectively, and $K_1$ is the amount of contrast taken up by cells per second in the voxel. $F_{ap}$, $F_{pvp}$ and $K_1$ have units of volume per second.

Given the long acquisition for observation of gadoxetic-acid uptake in liver parenchyma, after initial transient changes of contrast concentration in the plasma ($t > t_{plasma}$), the contrast concentration in the portal vein plasma should be equal to that in the arterial plasma, $C_{ap}(t)=C_{pvp}(t)$. Under this condition, Eq [3] may be re-written as:

$$V_{dis}\frac{dC_{dis}(t)}{dt} = F_t C_{ap}(t) - (F_t + K_1)C_{dis}(t) \text{ when } t > t_{plasma} \quad (4)$$

where $F_t$ is the total liver perfusion. Eq [4] may be re-written as:

$$C_{dis}(t) = \frac{F_t C_{ap}(t)}{F_t + K_1} - \frac{V_{dis}}{F_t + K_1}\frac{dC_{dis}(t)}{dt} \text{ when } t > t_{plasma} \quad (5)$$

Eq [5] expresses that the contrast concentration in the distribution space is determined by two terms. The first term is the dominant term. If $F_t \gg K_1$, the first term is approximately equal to $C_{ap}(t)$, the concentration of contrast agent in the arterial plasma. The second term is the ratio of the concentration change rate in the distribution space to the total perfusion plus the contrast uptake rate in liver cells. Eq [5] may be re-written as:

$$C_{dis}(t) = \frac{F_t C_{ap}(t)}{(F_t + K_1)} - \frac{F_t V_{dis}}{(F_t + K_1)^2}\frac{dC_{ap}(t)}{dt} + O\left(\frac{d^2 C_{ap}(t)}{dt^2}\right) + \ldots \text{ when } t > t_{plasma} \quad (6)$$

where the first term depends upon $C_{ap}$, the second term depends upon the first derivative of $C_{ap}$, the third term depends upon the second derivative of $C_{ap}$, and so on. If $F_t \gg K_1$, and the change in $C_{ap}$ (due to the cell uptake and clearance of the contrast agent from the system) after reaching $t_{plasma}$ is much slower than $F_t$, the result will be $C_{dis}(t)^{(0)} \approx C_{ap}(t)$.

After substituting $C_{dis}(t) \approx C_{ap}(t)$ into Eq [1] and re-arranging terms, the result is:

$$\underbrace{\frac{y}{(1-Hct)C_t(t)}}_{} = \underbrace{\frac{ax_1}{v_{dis}C_a(t)}}_{} + \underbrace{k_1 v_{dis}\int_0^t C_a(\tau)d\tau}_{bx_2} \quad (7)$$

where $v_{dis}$ is the fractional distribution volume, and the arterial plasma concentration $C_{ap}=C_a/(1-Hct)$ in which Hct is hematocrit. With $C_{ap}$ and $C_t$ known as measured from MR images that are sent from the MRI machine (or other liver image input system 117 as described above) to the liver function analysis server 140 and analyzed by the liver function quantification module 146, this becomes a linear problem, $y=ax_1+bx_2$, where $a=v_{dis}$ and $k_1=b/a$. Linear fitting allows for easily determining the linear coefficients of a and b and thereby the volume normalized contrast uptake rate $k_1$. Thus, the liver function quantification algorithm applies Eq [7] to the data vectors of $(1-Hct)C_t(t)$, $C_a(t)$ and $\int_0^t C_a(\tau)d\tau$ to determine the linear coefficients of a and b by performing a standard least-squares (LS) fitting. However, due to noise and the small number of measurements (for the temporally sparse sampled clinical multi-phase MRI data), maps of $k_1$ and $v_{dis}$ may be noisy. To address this issue, a spatial regularization term is added into the LS cost function $\Phi_{LS}$ as:

$$\Phi = \Phi_{LS} + \gamma R$$

where R may be an L2 or L1 operator to provide spatial regularization to enforce smoothness among neighboring voxels. Φ can be optimized iteratively following initiating the solution using standard LS fitting. Since the uptake rate $k_1$ is determined through a division by $v_{dis}$, small amounts of noise in this value can have a large impact in the calculated value for $k_1$. With regularization for this purpose our problem then takes the form $$\Phi = \Phi_{LS} + \frac{\gamma}{2}\left(\|b_u - u\|_p^p + \frac{1}{\sqrt{2}}\|b_v - v\|_p^p\right)$$

where p is 2 or 1 corresponding to the L2 or L1 operator, u and v are vectors corresponding to the $v_{dis}$ values of the orthogonal and diagonal neighbors of the current voxel, and $b_u$ and $b_v$ are vectors with all entries equal to the value of $v_{dis}$ in the current voxel. The use of the 8 connected neighborhood with diagonals allows increased isotropy in our regularization.

Optimization differs depending on whether the L2 or L1 operator is used (p=2, or p=1). The L2 operator gradient descent can be used to iteratively solve the problem. On the other hand, when the L1 operator is used, the function is not differentiable, so a subgradient projection can be used to iteratively solve the problem.

In some embodiments, the liver function quantification module 146 may also estimate the amount of error in approximating $C_{dis}$ as $C_{ap}(t)$. Using Eq [7], the $0^{th}$ order solution for $k_1^{(0)}$ and $v_{dis}^{(0)}$ may be obtained (the same parameters of $K_1^{(0)}$ and $V_{dis}^{(0)}$ but measured within the volume of interest ($V_t$)). Then, the error in $C_{dis}$ can be estimated to be:

$$\Delta C_{dis}(t) = -\frac{K_1^{(0)}}{F_t}C_{ap}(t) - \frac{V_{dis}^{(0)}}{F_t}\frac{dC_{ap}(t)}{dt} \quad \text{when } t > t_{plasma} \quad (8)$$

Typically the first term is negative and the second term is positive due to the decrease in $C_{ap}$ after $t > t_{plasma}$. $F_t$ can be estimated in the high temporal resolution DGAE MRI.

Accordingly, the liver function quantification algorithm includes the following for each voxel or portion of the patient's liver:

1. Obtain $C_{ap}(t)$ and $C_t(t)$ for the patient's liver using the MRI data
2. Calculate the integral of $C_{ap}(T)$ over time t
3. Generate three vectors of $C_t(t)$, $C_{ap}(t)$ and $\sim_0^t C_{ap}(\tau)d\tau$
4. Generate a linear liver pharmacokinetic model using standard LS fitting ($\Phi_{LS}$)
5. Add a spatial regularization term (γR) to the linear liver pharmacokinetic model ($\Phi_{LS}$) to enforce smoothness among neighboring voxels
6. Divide the two coefficients (b/a) resulting from minimizing the cost function (Φ) to calculate the contrast uptake rate metric ($k_1$)

Figure 4:
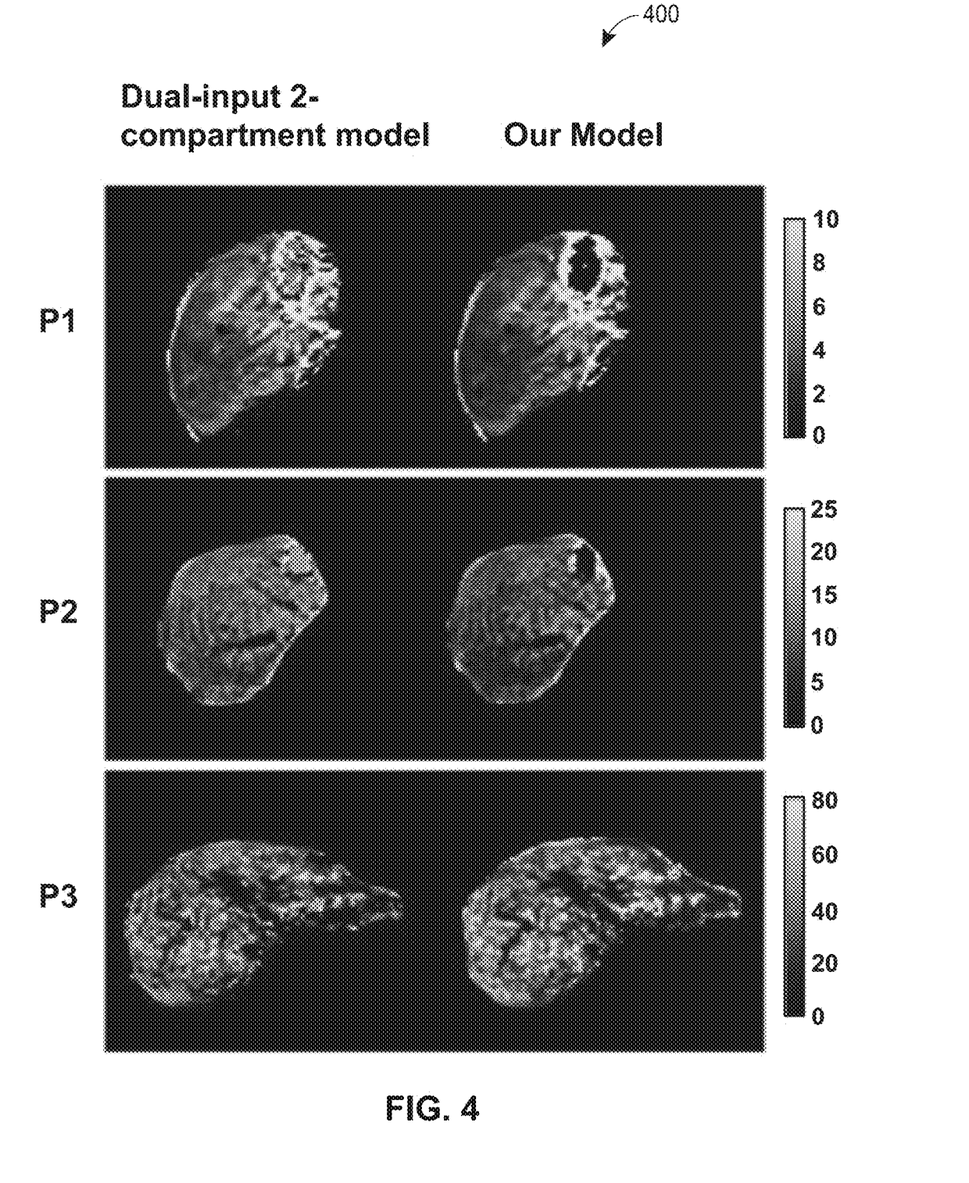
FIG. 4 illustrates exemplary slices of $k_1$ maps estimated by the dual-input two-compartment model (left column) and the liver function quantification algorithm described in this application (right column) for three patients (P1, P2, and P3).

To evaluate the accuracy of the liver function quantification algorithm, $k_1$ maps obtained from the high temporal resolution DGAE series using the dual-input two-compartment model are compared with $k_1$ maps obtained from the liver function quantification algorithm described in this application. The diagram 400 in FIG. 4 shows side-by-side $k_1$ maps estimated by the dual-input two-compartment model and by the liver function quantification algorithm for three different patients (P1, P2, and P3).

Figure 5:
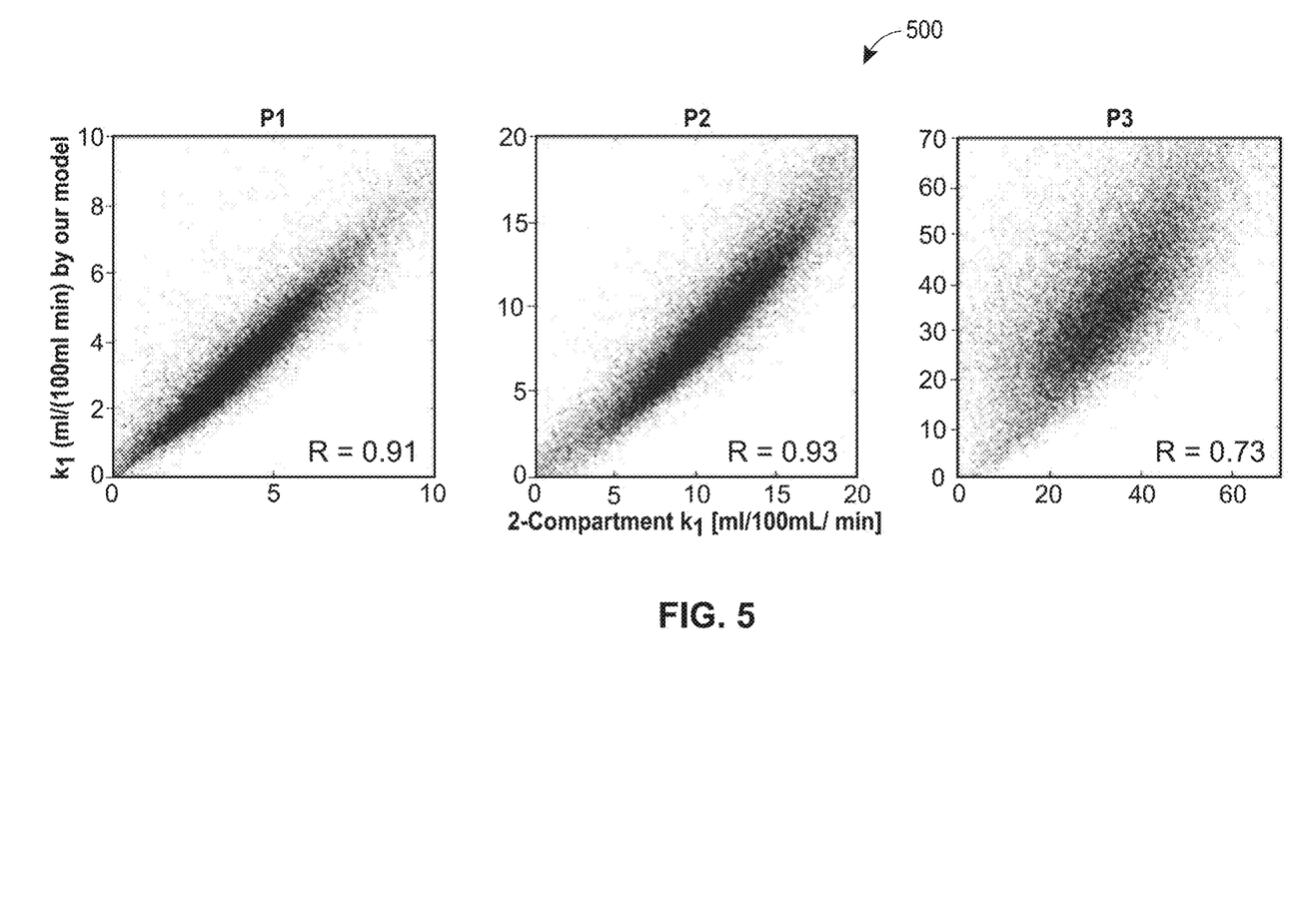
FIG. 5 illustrates exemplary scatter plots of $k_1$ values from a background region of the liver by the liver function quantification algorithm described in this application and the dual-input two-compartment model to demonstrate the correlation based on a sample of 25,000 voxels from each dataset. The $k_1$ scatter plots depicted in FIG. 4 are for the same three patients (P1, P2, and P3) as the slices of $k_1$ maps depicted in FIG. 3.

The cross correlation coefficients between $k_1$ values obtained by the dual-input two-compartment model and the liver function quantification algorithm for the three patients were 0.91, 0.93, and 0.73 as illustrated in diagram 500 of FIG. 5. Therefore, the $k_1$ maps produced by the liver function quantification algorithm closely resembles the $k_1$ maps estimated by the dual-input two-compartment model.

As mentioned above, the computational speed of the liver function quantification algorithm is approximately 1000 times faster than the standard dual-input two-compartment model. The liver function quantification algorithm uses temporally sparse-sampled multi-phase MRI with gadoxetic-acid injection which only requires 6 MRI scans at specific times (see above) while the standard dual-input two-compartment model uses high-temporal resolution dynamic contrast enhanced MRI which requires MRI scans every 3-4 seconds for up to 20 minutes (see above). Additionally, optimizing the 6 parameters in the dual-input two-compartment model is much more time consuming (see above) when compared to only having to determine the contrast uptake rate metric in the liver function quantification algorithm. Therefore, the liver function quantification algorithm is considerably faster than the standard dual-input two-compartment model.

The liver function quantification algorithm can provide a quantitative assessment of regional and global liver function of patients with intrahepatic cancer and cirrhosis from routine clinical gadoxetic-acid enhanced MRI. This algorithm can be used to support risk assessment of liver function for therapy selection and intervention/therapy planning.

Figure 6:
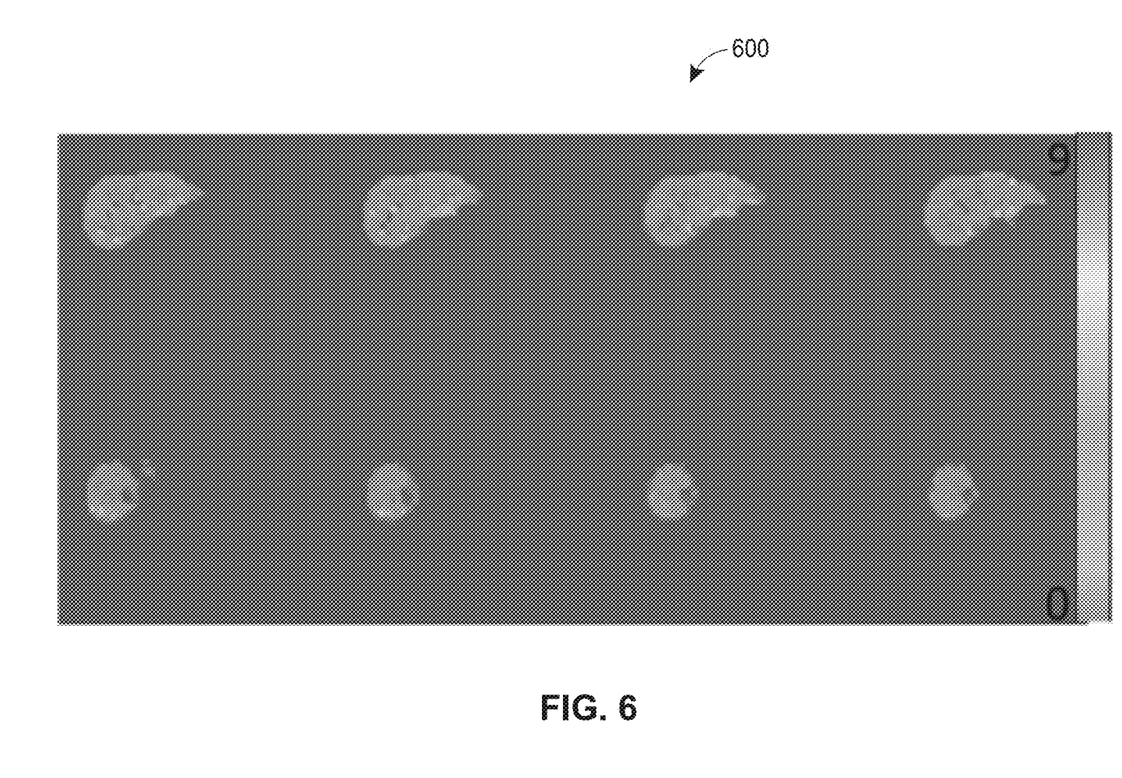
FIG. 6 illustrates exemplary liver slices of the $k_1$ maps (in a unit of ml/100 ml min)) quantified from the clinical 6-phase MRI scans of a patient with intrahepatic cancer prior to radiation therapy.

In some embodiments, the liver function quantification algorithm may be used in a single test to longitudinally document and monitor the regional and global liver function of a patient who has liver diseases and cancers and undergoes either intrahepatic interventions or a "see-and-wait" process (that requires to monitor the liver function periodically). The liver function quantification module 146 uses the liver function quantification algorithm to determine $k_1$ at various portions within a patient's liver (e.g., each voxel within an MR image) and generates a $k_1$ map of the patient's liver. The $k_1$ map may be provided to a network-enabled device 106-118 of a healthcare professional for further review. This is illustrated in diagram 600 of FIG. 6 which shows color-coded liver slices (shown here in shades of gray) of $k_1$ maps quantified from the clinical 6-phase MRI scans of a patient with intrahepatic cancer prior to radiation therapy. Each slice in diagram 600 is a slice of a regional liver function ($k_1$) map. Voxels or portions of the patient's liver having high $k_1$ values are color-coded with lighter shades of gray (red), while voxels or portions of the patient's liver having low $k_1$ values are color-coded with darker shades of gray (blue).

In other embodiments, the liver function quantification algorithm may be used in surgical planning. A liver surgeon may assess the current regional liver function distribution in the liver and the liver function volume of a patient by receiving $k_1$ maps at her network-enabled device 106-118 which are produced using the liver function quantification algorithm, as described in the previous example. Then, the surgeon can "actively" estimate the liver function volume preserve after a "resection" of a segment or lobe of the liver based upon the $k_1$ maps with a software interface. For example, the network-enabled device 106-118 may execute a liver function application which displays the $k_1$ maps and allows the liver surgeon to simulate resection of a segment or lobe of the liver. In some embodiments, the liver function quantification module 146 in the liver function analysis server 140 may then generate updated $k_1$ maps using the liver function quantification algorithm based on the resected segment or lobe of the liver. In other embodiments, the network-enabled device 106-118 generates the updated $k_1$ maps of the "un-resected" liver volume. The liver function volume preserve is then the sum of the $k_1 \Delta V$ over the "un-resected" liver volume.

Figure 7:
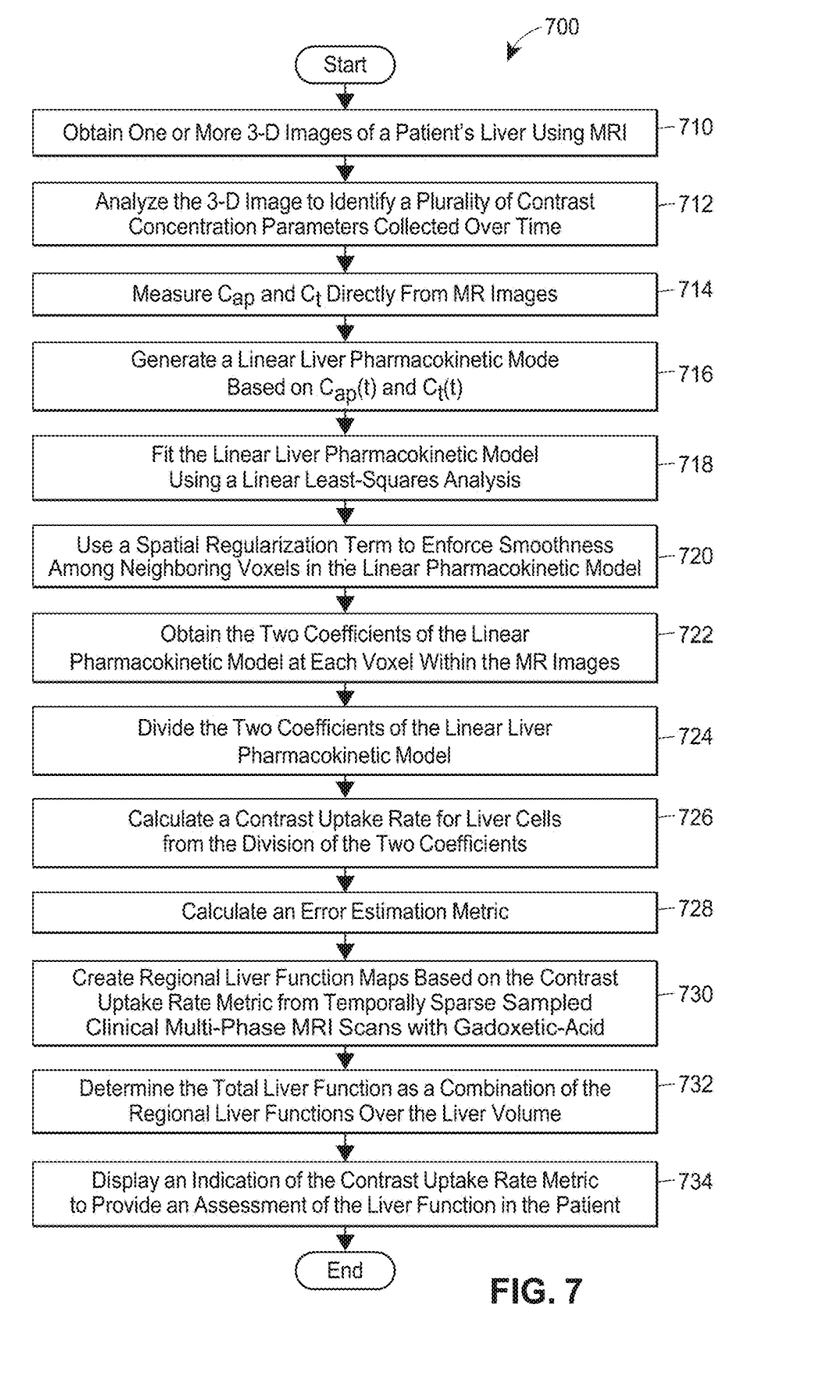
FIG. 7 illustrates a flow diagram representing an exemplary method for assessing the liver function of the patient using the liver function quantification algorithm described in this application.

FIG. 7 illustrates a flow diagram of an exemplary method 700 for assessing the liver function of the patient using the liver function quantification algorithm. The method 700 may be facilitated by the liver function quantification module 146 stored in the memory 150 located in the liver function analysis server 140. The liver function analysis server 140 may be connected, either wired or wirelessly, to an electronic device (such as one or more of the network-enabled devices 106-118) that may support the execution of the liver function quantification module 146.

The method 700 may begin when the liver function analysis server 140 obtains (block 710) one or more three-dimensional (3-D) images of a patient's liver collected by an MRI machine (or other liver image input system as described above 117). After the one or more 3-D images are obtained by the liver function analysis server 140, the liver function quantification module 146 may perform the following steps for each of the one or more 3-D images:

The liver function quantification module 146 may analyze (block 712) the 3-D image to identify a plurality of contrast concentration parameters collected over time. As part of the analysis, the liver function quantification module 146 may measure (block 714) $C_{ap}$ and $C_t$ directly from the MR images.

After $C_{ap}$ and $C_t$ are measured, the liver function quantification module 146 may generate (block 716) a linear liver pharmacokinetic model based on an independent variable $C_{ap}(t)$ and a dependent variable $C_t(t)$. The linear liver pharmacokinetic model may then be fitted (block 718) using a linear least-squares analysis of the independent and dependent variables. The liver function quantification module 146 may also use (block 720) a spatial regularization term to enforce smoothness among neighboring voxels.

The liver function module 146 may then obtain (block 722) the two coefficients (a and b as described above) of the linear liver pharmacokinetic model at each voxel within the MR images. The liver function quantification module 146 may then divide (block 724) the two coefficients of the linear liver pharmacokinetic model and may calculate (block 726) a contrast uptake rate for liver cells from the division of the two coefficients. The liver function quantification module 146 may also calculate (block 728) an error estimation metric in the distribution contrast concentration ($\Delta C_{dis}(t)$) by obtaining the $0^{th}$ order solution for contrast uptake rate ($k_1^{(0)}$) and a fractional distributional volume ($v_{dis}^{(0)}$) from the linear liver pharmacokinetic model.

Next the liver function quantification module 146 may create (block 730) one or more regional liver function maps based on the contrast uptake rate metric from temporally sparse sampled clinical multi-phase MRI scans with gadoxetic-acid. The liver function quantification module 146 may also quantify the single contrast uptake rate as the amount of contrast taken up by the liver cells per second in a voxel for each of the one or more regional liver function maps. Additionally, a single regional liver function map may be comprised of an array of voxels. Further, the liver function quantification module 146 may determine (block 732) the total liver function volume as a combination of the regional liver functions over the liver volume.

Finally, the liver function quantification module 146 may display (block 734) an indication of the contrast uptake rate metric to provide an assessment of the liver function in the patient to a healthcare professional. The liver function analysis server 140 may also transmit the indication of the contrast uptake rate metric to one or more of the network-enabled devices 106-118 to be stored or displayed on the device(s).

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein.

Additionally, certain embodiments are described herein as including logic or a number of routines, subroutines, applications, or instructions. These may constitute either software (e.g., code embodied on a machine-readable medium or in a transmission signal) or hardware. In hardware, the routines, etc., are tangible units capable of performing certain operations and may be configured or arranged in a certain manner. In example embodiments, one or more computer systems (e.g., a standalone, client or server computer system) or one or more hardware modules of a computer system (e.g., a processor or a group of processors) may be configured by software (e.g., an application or application portion) as a hardware module that operates to perform certain operations as described herein.

In various embodiments, a hardware module may be implemented mechanically or electronically. For example, a hardware module may comprise dedicated circuitry or logic that is permanently configured (e.g., as a special-purpose processor, such as a field programmable gate array (FPGA) or an application-specific integrated circuit (ASIC)) to perform certain operations. A hardware module may also comprise programmable logic or circuitry (e.g., as encompassed within a general-purpose processor or other programmable processor) that is temporarily configured by software to perform certain operations. It will be appreciated that the decision to implement a hardware module mechanically, in dedicated and permanently configured circuitry, or in temporarily configured circuitry (e.g., configured by software) may be driven by cost and time considerations.

Accordingly, the term "hardware module" should be understood to encompass a tangible entity, be that an entity that is physically constructed, permanently configured (e.g., hardwired), or temporarily configured (e.g., programmed) to operate in a certain manner or to perform certain operations described herein. Considering embodiments in which hardware modules are temporarily configured (e.g., programmed), each of the hardware modules need not be configured or instantiated at any one instance in time. For example, where the hardware modules comprise a general-purpose processor configured using software, the general-purpose processor may be configured as respective different hardware modules at different times. Software may accordingly configure a processor, for example, to constitute a particular hardware module at one instance of time and to constitute a different hardware module at a different instance of time.

Hardware modules can provide information to, and receive information from, other hardware modules. Accordingly, the described hardware modules may be regarded as being communicatively coupled. Where multiple of such hardware modules exist contemporaneously, communications may be achieved through signal transmission (e.g., over appropriate circuits and buses) that connect the hardware modules. In embodiments in which multiple hardware modules are configured or instantiated at different times, communications between such hardware modules may be achieved, for example, through the storage and retrieval of information in memory structures to which the multiple hardware modules have access. For example, one hardware module may perform an operation and store the output of that operation in a memory device to which it is communicatively coupled. A further hardware module may then, at a later time, access the memory device to retrieve and process the stored output. Hardware modules may also initiate communications with input or output devices, and can operate on a resource (e.g., a collection of information).

The various operations of example methods described herein may be performed, at least partially, by one or more processors that are temporarily configured (e.g., by software) or permanently configured to perform the relevant operations. Whether temporarily or permanently configured, such processors may constitute processor-implemented modules that operate to perform one or more operations or functions. The modules referred to herein may, in some example embodiments, comprise processor-implemented modules.

Similarly, the methods or routines described herein may be at least partially processor-implemented. For example, at least some of the operations of a method may be performed by one or more processors or processor-implemented hardware modules. The performance of certain of the operations may be distributed among the one or more processors, not only residing within a single machine, but deployed across a number of machines. In some example embodiments, the processor or processors may be located in a single location (e.g., within a home environment, an office environment or as a server farm), while in other embodiments the processors may be distributed across a number of locations.

The performance of certain of the operations may be distributed among the one or more processors, not only residing within a single machine, but deployed across a number of machines. In some example embodiments, the one or more processors or processor-implemented modules may be located in a single geographic location (e.g., within a home environment, an office environment, or a server farm). In other example embodiments, the one or more processors or processor-implemented modules may be distributed across a number of geographic locations.

Unless specifically stated otherwise, discussions herein using words such as "processing," "computing," "calculating," "determining," "presenting," "displaying," or the like may refer to actions or processes of a machine (e.g., a computer) that manipulates or transforms data represented as physical (e.g., electronic, magnetic, or optical) quantities within one or more memories (e.g., volatile memory, non-volatile memory, or a combination thereof), registers, or other machine components that receive, store, transmit, or display information.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

Some embodiments may be described using the expression "coupled" and "connected" along with their derivatives. For example, some embodiments may be described using the term "coupled" to indicate that two or more elements are in direct physical or electrical contact. The term "coupled," however, may also mean that two or more elements are not in direct contact with each other, but yet still co-operate or interact with each other. The embodiments are not limited in this context.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the description. This description, and the claims that follow, should be read to include one or at least one and the singular also includes the plural unless it is obvious that it is meant otherwise.

This detailed description is to be construed as providing examples only and does not describe every possible embodiment, as describing every possible embodiment would be impractical, if not impossible. One could implement numerous alternate embodiments, using either current technology or technology developed after the filing date of this application.

We claim:

1. A computer-implemented method for quantifying liver function in a patient, the method executed by one or more processors programmed to perform the method, the method comprising:

obtaining, at one or more processors, one or more three-dimensional (3-D) images of a patient's liver, the one or more 3-D images collected using magnetic resonance imaging (MRI), positron emission tomography (PET), or single-photon emission computed tomography (SPECT);

for each of the one or more 3-D images:
analyzing, by the one or more processors, the 3-D image to identify a plurality of contrast concentration parameters collected over time;
generating, by the one or more processors, a linear liver pharmacokinetic model using the plurality of contrast concentration parameters collected over time;
calculating, by the one or more processors, a contrast uptake rate metric for liver cells and a fractional distribution volume for blood based on the linear liver pharmacokinetic model, wherein the contrast uptake rate metric is indicative of liver function in the patient; and displaying, by the one or more processors, an indication of the contrast uptake rate metric to provide an assessment of the liver function in the patient to a healthcare professional.

2. The method of claim 1, wherein the plurality of contrast concentration parameters collected over time include at least one of: contrast concentration in arterial plasma ($C_{ap}(t)$) and contrast concentration in a total volume ($C_t(t)$).

3. The method of claim 2, wherein $C_{ap}$ and $C_t$ are measured directly from MRI, PET, or SPECT images.

4. The computer-implemented method of claim 1, wherein generating a linear liver pharmacokinetic model using a plurality of contrast concentration parameters collected over time comprises:
generating the linear liver pharmacokinetic model based on an independent variable $C_{ap}(t)$ and a dependent variable $C_t(t)$; and
fitting the linear liver pharmacokinetic model using a linear least-squares analysis of the independent and dependent variable over time.

5. The computer-implemented method of claim 4, further comprising:
obtaining two coefficients from the linear liver pharmacokinetic model, wherein the two coefficients of the linear liver pharmacokinetic model are obtained at each voxel within the MR image and wherein fitting the linear liver pharmacokinetic model using a linear least-squares analysis of the independent and dependent variable over time comprises:
using a spatial regularization term to enforce smoothness among neighboring voxels in the linear liver pharmacokinetic model.

6. The computer-implemented method of claim 5, wherein calculating a contrast uptake rate metric for liver cells and a fractional distribution volume for the blood based on the two coefficients of the linear liver pharmacokinetic model comprises:
dividing the two coefficients of the linear liver pharmacokinetic model wherein one coefficient is defined as the fractional distribution volume ($v_{dis}$).

7. The computer-implemented method of claim 1, wherein generating a linear liver pharmacokinetic model using a plurality of contrast concentration parameters collected over time comprises:
calculating an error estimation metric in the distribution contrast concentration ($\Delta C_{dis}(t)$) by obtaining the order solution for the contrast uptake rate ($k_1^{(0)}$) and the fractional distributional volume ($v_{dis}^{(0)}$) from the linear liver pharmacokinetic model.

8. The computer-implemented method of claim 1, wherein displaying an indication of the contrast uptake rate metric to provide an assessment of the liver function in the patient to a healthcare professional comprises:
creating one or more regional liver function maps based on the contrast uptake rate metric from temporally sparse sampled clinical multi-phase MRI scans with gadoxetic-acid; and
determining the total liver function as a combination of the regional liver functions over the liver volume.

9. The computer-implemented method of claim 8, wherein creating one or more regional liver function maps based on the contrast uptake rate metric from temporally sparse sampled clinical multi-phase MRI scans with gadoxetic-acid comprises:

quantifying, for each of the one or more regional liver function maps, the single contrast uptake rate as the amount of contrast taken up by the liver cells per second in a voxel.

10. The computer-implemented method of claim 9, wherein a single regional liver function map comprises an array of voxels.

11. A computing device for quantifying liver function in a patient, the computing device comprising:
a communication network,
one or more processors; and
a non-transitory computer-readable memory coupled to the one or more processors and storing thereon instructions that, when executed by the one or more processors, cause the computing device to:
obtain one or more three-dimensional (3-D) images of a patient's liver, the one or more 3-D images collected using magnetic resonance imaging (MRI), positron emission tomography (PET), or single-photon emission computed tomography (SPECT);
for each of the one or more 3-D images:
analyze the 3-D image to identify a plurality of contrast concentration parameters collected over time;
generate a linear liver pharmacokinetic model using the plurality of contrast concentration parameters collected over time;
calculate a contrast uptake rate metric for liver cells and a fractional distribution volume for blood based on the linear liver pharmacokinetic model, wherein the contrast uptake rate metric is indicative of liver function in the patient; and
display an indication of the contrast uptake rate metric to provide an assessment of the liver function in the patient to a healthcare professional.

12. The computing device of claim 11, wherein the plurality of contrast concentration parameters collected over time include at least one of: contrast concentration in arterial plasma ($C_{ap}(t)$) and contrast concentration in a total volume ($C_t(t)$).

13. The computing device of claim 11, wherein $C_{ap}$ and $C_t$ are measured directly from MRI, PET, or SPECT images.

14. The computing device of claim 11, wherein to generate a linear liver pharmacokinetic model using a plurality of contrast concentration parameters collected over time, the instructions cause the computing device to:
generate the linear liver pharmacokinetic model based on an independent variable $C_{ap}(t)$ and a dependent variable $C_t(t)$; and
fit the linear liver pharmacokinetic model using a linear least-squares analysis of the independent and dependent variable over time.

15. The computing device of claim 14, wherein the instructions cause the computing device to:
obtain two coefficients from the linear liver pharmacokinetic model, wherein the two coefficients of the linear liver pharmacokinetic model are obtained at each voxel within the MR image and wherein to fit the linear liver pharmacokinetic model using a linear least-squares analysis of the independent and dependent variable over time, the instructions cause the computing device to:
use a spatial regularization term to enforce smoothness among neighboring voxels in the linear liver pharmacokinetic model.

16. The computing device of claim 15, wherein to calculate a single contrast uptake rate metric for liver cells and a fractional distribution volume for blood based on the two coefficients of the linear liver pharmacokinetic model, the instructions cause the computing device to:

divide the two coefficients of the linear liver pharmacokinetic model wherein one coefficient is defined as the fractional distribution volume ($v_{dis}$).

17. The computing device of claim 11, wherein to generate a linear liver pharmacokinetic model using a plurality of contrast concentration parameters collected over time, the instructions cause the computing device to:

calculate an error estimation metric in the distribution contrast concentration ($\Delta C_{dis}(t)$) by obtaining the $0^{th}$ order solution for the contrast uptake rate ($k_1^{(0)}$) and the fractional distributional volume ($v_{dis}^{(0)}$) from the linear liver pharmacokinetic model.

18. The computing device of claim 11, wherein to display an indication of the contrast uptake rate metric to provide an assessment of the liver function in the patient to a healthcare professional, the instructions cause the computing device to:

create one or more regional liver function maps based on the contrast uptake rate metric from temporally sparse sampled clinical multi-phase MRI scans with gadoxetic-acid; and determine the total liver function as a combination of the regional liver functions over the liver volume.

19. The computing device of claim 18, wherein to create one or more regional liver function maps based on the contrast uptake rate metric from temporally sparse sampled clinical multi-phase MRI scans with gadoxetic-acid, the instructions cause the computing device to:

quantify, for each of the one or more regional liver function maps, the single contrast uptake rate as the amount of contrast taken up by the liver cells per second in a voxel.

20. The computing device of claim 19, wherein a single regional liver function map comprises an array of voxels.

* * * * *